(12) United States Patent
Hasebe et al.

(10) Patent No.: US 8,198,330 B2
(45) Date of Patent: Jun. 12, 2012

(54) THERAPEUTIC OR PROPHYLACTIC AGENT FOR DIABETES, OBESITY, DYSLIPIDEMIA OR METABOLIC SYNDROME COMPRISING BENZYLAMINE DERIVATIVE OR PHARMACEUTICALLY ACCEPTABLE ACID ADDITION SALT THEREOF

(75) Inventors: Ko Hasebe, Kanagawa (JP); Satoru Yoshikawa, Kanagawa (JP); Hideki Kozono, Chiba (JP); Seiji Okazaki, Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/056,201

(22) PCT Filed: Jul. 31, 2009

(86) PCT No.: PCT/JP2009/063632
§ 371 (c)(1),
(2), (4) Date: Jan. 27, 2011

(87) PCT Pub. No.: WO2010/013798
PCT Pub. Date: Feb. 4, 2010

(65) Prior Publication Data
US 2011/0124733 A1      May 26, 2011

(30) Foreign Application Priority Data

Jul. 31, 2008 (JP) ................. 2008-198047

(51) Int. Cl.
*A61K 31/18* (2006.01)
*C07C 307/00* (2006.01)
*A61P 3/00* (2006.01)
(52) U.S. Cl. .......................... 514/605; 564/99
(58) Field of Classification Search .................. 514/605; 564/99
See application file for complete search history.

(56) References Cited

U.S. PATENT DOCUMENTS

| 3,341,584 A | 9/1967 | Larsen et al. |
| 5,776,983 A | 7/1998 | Washburn et al. |
| 2002/0068751 A1 | 6/2002 | Coghlan et al. |
| 2007/0078184 A1 | 4/2007 | Kobayashi et al. |
| 2010/0099769 A1 | 4/2010 | Hayashi et al. |

FOREIGN PATENT DOCUMENTS

| EP | 2 119 700 A1 | 11/2009 |
| JP | 7-206806 A | 8/1995 |
| WO | 02/06255 A2 | 1/2002 |
| WO | 2005/040093 A1 | 5/2005 |
| WO | 2008/093767 A1 | 8/2008 |

OTHER PUBLICATIONS

Takeuchi et al., *Folia Pharmacologica Japonica*, 2006, vol. 128, pp. 37-41 and 1 page English Abstract).

Peter et al., "Organic Reaction," *Wiley & Sons*, 1948, vol. 4, p. 174-255 and summary.
Peter et al., "Organic Reaction," *Wiley & Sons*, 1948, 1953, vol. 7, pp. 263-326 and summary.
Hoffman et al., "Comparative Pharmacology of Human β-Adrenergic Receptor Subtypes—Characterization of Stably Transfected Receptors in CHO Cells," *Naunyn Schmiedeberg's Arch. Pharmcol.*, 2004, vol. 369, No. 2, pp. 151-159.
Fieser, "Fieser and Fieser's Reagent for Organic Synthesis," *Wiley & Sons*, 1967, vol. 1, pp. 963-964 and summary.
Fieser, "Fieser and Fieser's Reagent for Organic Synthesis," *Wiley & Sons*, 1986, vol. 12, p. 65 and summary.
J.R.S. Arch et al., "$β_3$ and Atypical β-Adrenoceptors," *Medicinal Research Reviews*, vol. 13, No. 6, 1993, pp. 663-729.
Archana Chaudhry et al., "Influence of Cell Type upon the Desensitization of the $β_3$-Adrenergic Receptor[1]" *The Journal of Pharmacology and Experimental Therapeutics*, vol. 271, No. 3, 1994, pp. 1253-1258.
Toshiya Tanaka et al., "Activation of peroxisome proliferator-activated receptor δ induces fatty acid β-oxidation in skeletal muscle and attenuates metabolic syndrome," *PNAS*, vol. 100, No. 26, Dec. 23, 2003, pp. 15924-15929.
Maria Sörhede Winzell et al., "The High-Fat Diet-Fed Mouse A Model for Studying Mechanisms and Treatment of Impaired Glucose Tolerance and Type 2 Diabetes," *Diabetes*, vol. 53, Supplement 3, Dec. 2004, pp. S215-S219.
Kazuo Takahashi et al., "Guidelines for obesity and metabolic syndrome," *Igakuno Ayumi*, vol. 213, No. 6, 2005, pp. 549-554 (partial translation).

(Continued)

*Primary Examiner* — Sreeni Padmanabhan
*Assistant Examiner* — Sahar Javanmard
(74) *Attorney, Agent, or Firm* — DLA Piper LLP (US)

(57) ABSTRACT

A method of treatment or prophylaxis of diabetes, obesity, dyslipidemia or metabolic syndrome includes administering an effective amount of a benzylamine derivative represented by Formula (I):

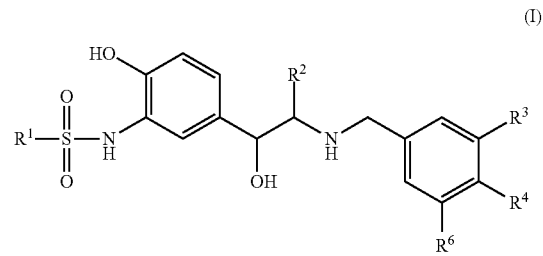

(I)

wherein, $R^1$ represents an alkyl group having 1 to 6 carbon atoms; $R^2$ represents an alkyl group having 1 to 6 carbon atoms; $R^3$ and $R^5$ each independently represent a halogen atom, an alkyl group having 1 to 6 carbon atoms, a haloalkyl group having 1 to 6 carbon atoms or an alkoxy group having 1 to 6 carbon atoms; and $R^4$ represents a hydrogen atom or an alkoxy group having 1 to 6 carbon atoms, or a pharmaceutically acceptable acid addition salt thereof.

13 Claims, 1 Drawing Sheet

OTHER PUBLICATIONS

Atsuhito Saiki et al., "The role of anti-obesic in the treatment of metabolic syndrome," Igakuno Ayumi, vol. 213, No. 6, 2005, pp. 643-649 (partial translation).

Masakazu Hirata et al., "Metabolic Syndrome: Current Diagnostic Criteria and its Pathophysiology," Saishin Igaku, vol. 61, No. 3 (Special Issue), 2006, pp. 579-590 (partial translation).

Takeuchi et al., Folia Pharmacol. Jpn., vol. 128, 2006, pp. 37-41.

"Medical Drugs 2008," Japan Pharmaceutical Information Center Ed., 2007, pp. 2428-2429 (partial translation).

Helio C. Salgado et al., "Baroreflex responses to electrical stimulation of aortic depressor nerve in conscious SHR," Am. J. Physiol. Heart Circ. Physiol, vol. 292, 2007, pp. H593-H600.

Makoto Kinoshita, "Content of the New Guideline," Saishin Igaku, vol. 63, No. 2, 2008, pp. 7(155)-12(160) (partial translation).

Takuya Okada et al., "Strategy for the Treatment of the Metabolic Syndrome," Saishin Igaku, vol. 63, No. 2, 2008, pp. 114(262)-118(266) (partial translation).

"Diabetes Treatment Guide 2008-2009," Japan Diabetes Society Ed., 2008, pp. 44-59 (partial translation).

W.N. Washburn et al., "Beta 3 Agonists. Part 1: Evolution from Inception to BMS-194449," Bioorganic & Medicinal Chemistry Letters, vol. 11, 2001, pp. 3035-3039.

Hiroshi Harada et al., "Discovery of a Novel and Potent Human and Rat $\beta_3$-Adrenergic Receptor Agonist, [3-[2$R$)-[[(2$R$)-(3-Chlorophenyl)-2-hydroxyethyl]amino]propyl]-1$H$-indol-7-yloxy]acetic Acid," Chem. Pharm. Bull., vol. 53, No. 2, 2005, pp. 184-198.

Jean-Pierre Revelli et al., "Targeted Gene Disruption Reveals a Leptin-independent Role for the Mouse $\beta_3$-Adrenoceptor in the Regulation of Body Composition," J. Clin. Invest., vol. 100, No. 5, Sep. 1997, pp. 1098-1106.

A.V. Gavai et al., "BMS-196085: A Potent and Selective Full Agonist of the Human $\beta_3$ Adrenergic Receptor," Bioorganic & Medicinal Chemistry Letters, vol. 11, 2001, pp. 3041-3044.

Ralph Howe, "$\beta_3$-Adrenergic agonists," Drugs of the Future, vol. 18, No. 6, 1993, pp. 529-549.

Sum, F-W. et al., "Cyclic Amine Sulfonamides as Linkers in the Design and Synthesis of Novel Human β-3 Adrenergic Receptor Agonists," *Bioorganic & Medicinal Chemistry Letters*, Jan. 2003, vol. 13, No. 13, pp. 2191-2194.

THERAPEUTIC OR PROPHYLACTIC AGENT FOR DIABETES, OBESITY, DYSLIPIDEMIA OR METABOLIC SYNDROME COMPRISING BENZYLAMINE DERIVATIVE OR PHARMACEUTICALLY ACCEPTABLE ACID ADDITION SALT THEREOF

RELATED APPLICATIONS

This is a §371 of International Application No. PCT/JP2009/063632, with an international filing date of Jul. 31, 2009 (WO 2010/013798 A1, published Feb. 4, 2010), which is based on Japanese Patent Application No. 2008-198047, filed Jul. 31, 2008, the subject matter of which is incorporated by reference.

TECHNICAL FIELD

This disclosure relates to a therapeutic or prophylactic agent to diabetes, obesity, dyslipidemia or metabolic syndrome, which comprises a benzylamine derivative represented by formula or a pharmaceutically acceptable acid addition salt thereof.

BACKGROUND

Diabetes is a chronic disease caused by dysbolism leading to chronic hyperglycemic state by insufficient action of insulin. Diabetes is grouped into Type 1 diabetes characterized by insufficient secretion of insulin and Type 2 diabetes characterized by lowered secretion of insulin and lowered sensitivity (insulin resistance). In particular, Type 2 diabetes, which accounts for 90 to 95% of diagnosed diabetes, is said to be closely correlated with contemporary life-style diseases, such as obesity, hypertension, hyperlipemia and metabolic syndrome.

Known diabetes drugs include sulfonylureas, phenylalanine derivatives, α-glucosidase inhibitors, biguanides, thiazolidine derivatives and the like, but use of these drugs is restricted, because of accompanied adverse reaction such as severe hypoglycemia, gastrointestinal tract disorder, liver function disorder or lactic acidosis. In addition, sulfonylureas and thiazoline derivatives are known to accelerate increase of body weight (Japan Diabetes Society Ed., "Diabetes Treatment Guide 2008-2009," 2008).

Obesity, which is in the state where energy is stored abnormally in adipose tissue by overeating and lack of exercise, can cause Type 2 diabetes and also hypertension, heart disease and others.

Anti-obesity drugs include Mazindol, Orlistat, Rimonabant and the like. Mazindol has primary pharmacologic actions of central suppression of feeding and acceleration of heat production in peripheral organs, but is often accompanied with central adverse reactions such as nausea, headache and dizziness and, thus, strict control is needed for its use. Orlistat suppresses fat absorption and thus leads to decrease of body weight by inhibiting lipases, but it also inhibits absorption of lipophillic vitamins and, thus, vitamins should be supplemented, as needed. Rimonabant suppresses appetite and leads to decrease of body weight by interaction with cannabinoid 1 receptor, but has a problem of central adverse reactions such as dizziness, nausea and headache. These anti-obesity drugs have not only action to reduce body weight but also various disadvantages and adverse reactions and, for that reason, there exists a need for development of an anti-obesity drug that is more effective and superior in efficiency in use (Japan Pharmaceutical Information Center Ed., "Medical Drugs 2008," 2007, Takahashi et al., Igakuno Ayumi, Vol. 213, No. 6, 2005, p 549 and Saiki et al., Igakuno Ayumi," Vol. 213, No. 6, 2005, p 643).

Dyslipidemia is a disease accompanied with abnormality in blood cholesterol and tri-glyceride levels. Dyslipidemia results in arteriosclerosis, further leading to increase of the risks of coronary disease such as angina cordis and myocardial infarction. Anti-dyslipidemia drugs are drugs for reduction of the blood triglyceride and LDL cholesterol levels that are important for prevention of coronary diseases (Kinoshita, Saishin Igaku, Vol. 63, No. 2, 2008, p 7).

Anti-dyslipidemia drugs include statins (HMG-CoA reductase inhibitor) such as pravastatin and atrovastatin; bile acid absorbents such as cholestyramine and cholestimide; fibrates such as clofibrate and bezafibrate; and the like. Statins occasionally cause adverse reactions such as digestive organ symptoms and rhabdomyolysis. Bile acid absorbents have adverse reactions such as constipation and abdominal bloating and occasionally inhibit absorption of drugs used in combination. Fibrates should be used carefully with caution to the adverse reactions such as rhabdomyolysis and liver function disorder. All of these anti-dyslipidemia drugs have action to decrease serum triglyceride or cholesterol level, but, in fact, they also have various disadvantages and adverse reactions (Japan Pharmaceutical Information Center Ed., "Medical Drugs 2008," 2007).

Metabolic syndrome is a syndrome in combination of some of abdominal obesity, hypertriglyceridemia, hypo-HDL-cholestrolemia, hyperglycemia and hypertension, and it is considered to be a syndrome higher in the risk of arteriosclerotic diseases, because these symptoms in combination leads to increase of the risk of arteriosclerotic diseases.

As for the diagnostic standard of metabolic syndrome, for example, National Cholesterol Education Program (hereinafter, NCEP) in 2001 defines, as the metabolic syndrome, a syndrome that have values higher than standards at least in three risk factors among the risk factors 1 to 5 shown in Table 1. The International Diabetes Federation (hereinafter, IDF) and the Examination Committee of Criteria for Obesity Disease in Japan (joint committee of eight academic societies including Japan Atherosclerosis Society, Japan Diabetes Society and others) define, as the metabolic syndrome, a syndrome showing abdominal obesity as essential item and additionally multiple items selected from hypertriglyceridemia, hypo-HDL-cholesterolemia, hypertension and hyperglycemia. Because the risk factors are treated only individually in chemical treatment of metabolic syndrome, there exists a need for a drug that is effective to multiple risk factors even as a single drug (Hirata et al., Saishin Igaku, Vol. 61, No. 3 (Special Issue), 2006, p 579 and Okada et al., Saishin Igaku, Vol. 63, No. 2, 2008, p 262).

TABLE 1

Standard for diagnosis of metabolic syndrome (NCEP Standard)

| Risk factor | | Standard |
|---|---|---|
| 1. Abdominal circumference | male | >102 cm |
| | female | >88 cm |
| 2. Triglyceride | | ≧150 mg/dl |
| 3. HDL cholesterol | male | <40 mg/dl |
| | female | <50 mg |
| 4. Blood pressure | | |
| Systolic blood pressure and/or | | ≧130 mmHg |
| Diastolic blood pressure | | ≧85 mmHg |
| 5. Fasting blood sugar | | ≧110 mg/dl |

Under the circumstance above, β3 adrenoreceptor agonists have been proposed as a new drug candidate to type 2 diabetes and obesity (Washburn et al., Bioorg. Med. Chem. Lett., Vol. 11, 2001, p 3035 and Harada et al., Chem. Pharm. Bull., Vol. 53, 2005, p 184). The β3 adrenoreceptors present in the fat cells of rodents and humans are suggested as having an important role in regulation of fat decomposition and heat production (Howe, Drug Future, Vol. 18, 1993, p 529 and Arch et al., J. Med. Res. Rev., Vol. 13, 1993, p 663). Functional deterioration of β3 adrenoreceptor results, for example, in accumulation of body fat and, thus, its correlation with development of obesity is suggested (Revelli et al., J. Clin Invest., Vol. 100, 1997, P 1098). However, development of a β3 adrenoreceptor agonist as diabetes drug is so far unfruitful, because of the adverse reactions on the cardiovascular system.

JP-A 7-206806 discloses a β3 adrenoreceptor agonist (amine derivative). However, there is no disclosed pharmacological data showing the efficacy thereof to diabetes and obesity.

Washburn et al., Bioorg. Med. Chem. Lett., Vol. 11, 2001, p 3035 discloses the following benzylamine derivative (1) as a β3 adrenoreceptor agonist. However, the data available concerning the efficacy thereof to diabetes and obesity is only limited to the action of decomposing free fatty acids.

Formula 1

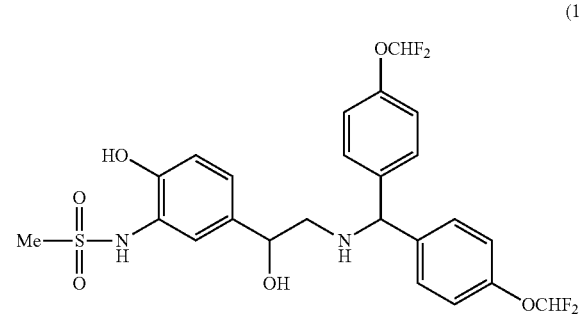

(1)

No drug is developed from the benzylamine derivative (1) above and analogous benzylamine derivatives, which are β3 adrenoreceptor agonists, because there are adverse reactions on the cardiovascular system (prolongation of QT interval and increase of heart rate) (Washburn et al., Bioorg. Med. Chem. Lett., Vol. 11, 2001, p 3035 and Gavai et al., Bioorg. Med. Chem. Lett., Vol. 11, 2001, p 3041).

Alternatively, U.S. Pat. No. 3,341,584 discloses a wide range of compounds including part of the benzylamine derivatives (1) above. However, usefulness of these compounds to diabetes, obesity, dyslipidemia or metabolic syndrome is currently unknown.

Thus, it could be helpful to provide a therapeutic or prophylactic agent for diabetes, obesity, dyslipidemia or metabolic syndrome, which can exhibit significant efficacy at lower dose and does not have an increase of heart rate or a prolongation of QT interval which is an adverse side effect on the cardiovascular system.

SUMMARY

We discovered that in in-vivo studies by using Type 2 diabetes model mice (KK/Ay mice) and diabetes-obesity model mice (Diet Induced Obesity mice: hereinafter, referred to as DIO mice), a new benzylamine derivative superior in selectivity to β3 adrenoreceptor has a favorable efficacy to diabetes, obesity, dyslipidemia or metabolic syndrome, but does not have the adverse reactions on the cardiovascular system (prolongation of QT interval and increase of heart rate), which is a serious problem associated with chemical therapy of chronic diseases, and made this disclosure.

Thus, we provide a therapeutic or prophylactic agent to diabetes, obesity, dyslipidemia or metabolic syndrome, which comprises a benzylamine derivative represented by General Formula (I):

Formula 2

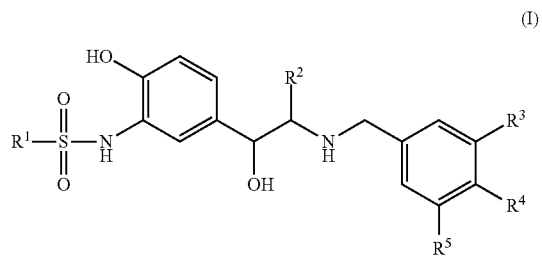

(I)

wherein, $R^1$ represents an alkyl group having 1 to 6 carbon atoms; $R^2$ represents an alkyl group having 1 to 6 carbon atoms; $R^3$ and $R^5$ each independently represent a halogen atom, an alkyl group having 1 to 6 carbon atoms, a haloalkyl group having 1 to 6 carbon atoms or an alkoxy group having 1 to 6 carbon atoms; and $R^4$ represents a hydrogen atom or an alkoxy group having 1 to 6 carbon atoms, or a pharmaceutically acceptable acid addition salt thereof.

In the therapeutic or prophylactic agent above, $R^1$ is preferably methyl, ethyl, propyl, isopropyl or tert-butyl; $R^2$ is preferably methyl, ethyl, propyl or isopropyl; $R^3$ and $R^5$ are each independently preferably methyl, ethyl, fluoromethyl, difluoromethyl, trifluoromethyl, methoxy, ethoxy or chloro; and $R^4$ is preferably a hydrogen atom, methoxy, ethoxy, propoxy or iso-propoxy.

More preferably in the therapeutic or prophylactic agent above, $R^2$ is methyl; $R^3$ and $R^5$ are each independently methyl, ethyl, fluoromethyl, difluoromethyl, trifluoromethyl, methoxy, ethoxy or chloro; and $R^4$ is a hydrogen atom, methoxy, ethoxy, propoxy or isopropoxy, and more preferably, $R^1$ and $R^2$ are methyl; $R^3$ and $R^5$ are each independently methyl, trifluoromethyl, methoxy or chloro; and $R^4$ is a hydrogen atom or methoxy.

Still more preferably in the therapeutic or prophylactic agent above, $R^1$ and $R^2$ are methyl; $R^3$ and $R^5$ are simultaneously methyl, trifluoromethyl, methoxy or chloro; and $R^4$ is a hydrogen atom.

We also provide a method for therapy or prophylaxis of diabetes, obesity, dyslipidemia or metabolic syndrome, comprising administering an effective amount of the above-described therapeutic or prophylactic agent.

Further, we provide use of a benzylamine derivative represented by General Formula (I) above or a pharmaceutically acceptable acid addition salt thereof in production of a pharmaceutical for treatment or prevention of diabetes, obesity, dyslipidemia or metabolic syndrome.

The therapeutic or prophylactic agent exhibits distinctive therapeutic or preventive effect to diabetes, obesity, dyslipidemia or metabolic syndrome without adverse reactions to the cardiovascular system such as increase of heart rate and prolongation of QT interval.

DETAILED DESCRIPTION

Figure 1:
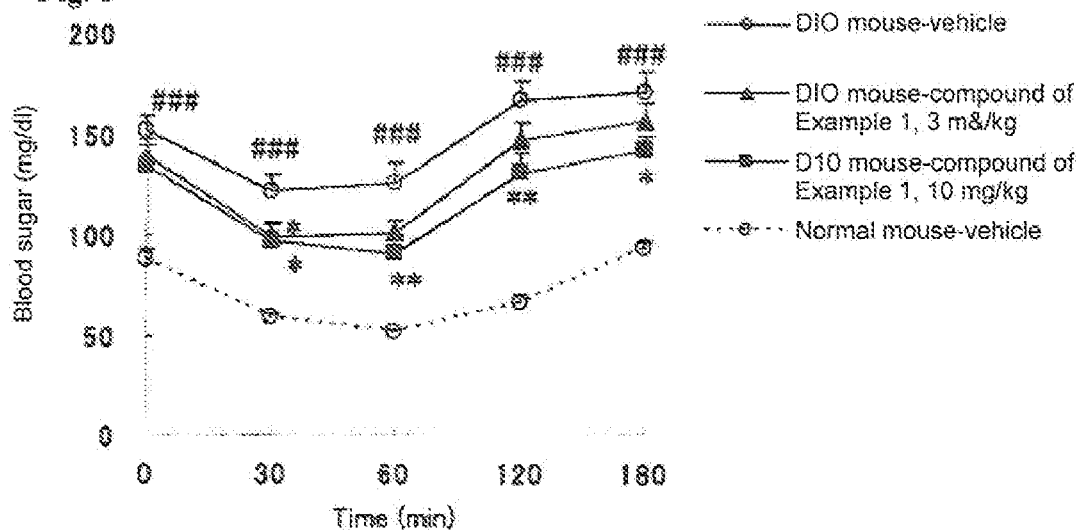
FIG. 1 is a chart showing the influence of the compound of Example 1 on the blood sugar-reducing action after administration of insulin. The abscissa shows the time (minutes) after insulin administration, while the ordinate shows the blood sugar level of mouse. ###$p<0.001$ vs. normal mice (vehicle administered group), *$p<0.05$ and **$p<0.01$ vs. DIO mice (vehicle administered group) (parametric Williams test, respectively tested at each point).

The terms used below are defined as follows, unless specified otherwise.

The term "alkyl" group means a monovalent linear or branched saturated hydro-carbon group consisting of carbon and hydrogen atoms.

The term "alkoxy" group means an —OR group, in which R is the alkyl as defined herein.

The term "halogen" atom means fluoro, chloro, bromo or iodo.

The term "haloalkyl" group means an alkyl as defined herein of which hydrogen atoms are replaced with the one or more halogen atoms as defined herein at an arbitrary position.

The term "diabetes" means a disease diagnosed as diabetes according to the diagnostic standard, for example, of WHO (World Health Organization), Japan Diabetes Society, American Diabetes Association or European Association for the Study of Diabetes and include Type 1 diabetes, Type 2 diabetes, pregnancy diabetes, and the like. The Type 2 diabetes is characterized by its resistance to the action of insulin, i.e., "insulin resistance."

The "insulin resistance" means a disease diagnosed as insulin resistance, based on the insulin resistance index (fasting blood sugar (mg/dL)×fasting insulin (μU/mL)÷405) or on the results obtained by examination by glucose clamp method or the like and includes syndrome X additionally. In addition to Type 2 diabetes, diseases with "insulin resistance" include, for example, fatty liver, particularly NAFLD (non-alcoholic fatty liver disease), NASH (non-alcoholic steatohepatitis), coronary heart diseases (CHDs), arteriosclerotic diseases, hyperglycemia, lipodosis, impaired glucose tolerance, hypertension, hyperlipemia, diabetes complications, pregnancy diabetes, polycystic ovary syndrome and the like.

The term "dyslipidemia" means a disease diagnosed as dyslipidemia according to the diagnostic standard, for example, of WHO or Japan Atherosclerosis Society and includes hyperlipemia, hypercholestrolemia, hyper-LDL-cholestrolemia, hypo-HDL-cholestrolemia, hypertriglyceridemia and the like.

The term "obesity" means a disease diagnosed as obesity according to the diagnostic standard, for example, of WHO or Japan Society for the Study of Obesity and include "overweight" and others.

The term "metabolic syndrome" means a disease diagnosed as metabolic syndrome according to the diagnostic standard, for example, of WHO, NCEP, IDF or the Committee for Diagnostic Standard of Metabolic Syndrome in Japan Atherosclerosis Society.

The term "therapeutic or prophylactic agent" includes an agent used for treatment or prevention and also an agent used both for treatment and prevention simultaneously.

The therapeutic or prophylactic agent for diabetes, obesity, dyslipidemia or metabolic syndrome is characterized by containing a benzylamine derivative represented by General Formula (I):

Formula 3

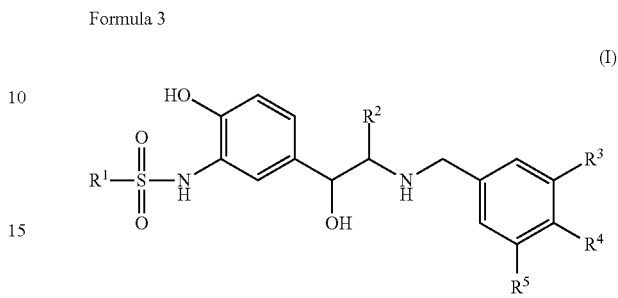

(I)

wherein, $R^1$ represents an alkyl group having 1 to 6 carbon atoms; $R^2$ represents an alkyl group having 1 to 6 carbon atoms; $R^3$ and $R^5$ each independently represent a halogen atom, an alkyl group having 1 to 6 carbon atoms, a haloalkyl group having 1 to 6 carbon atoms or an alkoxy group having 1 to 6 carbon atoms; and $R^4$ represents a hydrogen atom or an alkoxy group having 1 to 6 carbon atoms, or a pharmaceutically acceptable acid addition salt thereof.

In the benzylamine derivatives represented by General Formula (I), examples of the alkyl groups having 1 to 6 carbon atoms of $R^1$, $R^2$, $R^3$ and $R^5$ include, but are not limited to, methyl, ethyl, propyl, isopropyl, butyl, sec-butyl, tert-butyl, pentyl, hexyl and the like.

Examples of the haloalkyl groups having 1 to 6 carbon atoms of $R^3$ and $R^5$ include, but are not limited to, fluoromethyl, chloromethyl, difluoromethyl, dichloromethyl, trifluoro-methyl, trichloromethyl, 2,2,2-trifluoroethyl, 2,2,2-trichloroethyl and the like.

Examples of the alkoxy groups having 1 to 6 carbon atoms of $R^3$, $R^4$ and $R^5$ include, but are not limited to, methoxy, ethoxy, propoxy, isopropoxy, butoxy, tert-butoxy and the like.

Examples of the halogen atoms of $R^3$ and $R^5$ include, but are not limited to, fluoro, chloro, bromo, iodo and the like.

Typical favorable examples of $R^1$ to $R^5$ are shown below. However, these groups are only typical examples, and $R^1$ to $R^5$ are not limited to these groups.

$R^1$ is preferably methyl, ethyl, propyl, isopropyl or tert-butyl, more preferably methyl or isopropyl, and still more preferably methyl.

$R^2$ is preferably methyl, ethyl, propyl or isopropyl, more preferably, methyl, ethyl or propyl, and still more preferably methyl.

$R^3$ and $R^5$ are each independently, preferably methyl, ethyl, fluoromethyl, difluoro-methyl, trifluoromethyl, methoxy, ethoxy or chloro, more preferably methyl, trifluoromethyl, methoxy or chloro, and $R^3$ and $R^5$ are still more preferably simultaneously methyl, trifluoro-methyl, methoxy or chloro.

$R^4$ is preferably a hydrogen atom, methoxy, ethoxy, propoxy or isopropoxy, more preferably a hydrogen atom, methoxy or ethoxy, and still more preferably a hydrogen atom or methoxy.

The benzylamine derivative represented by General Formula (I) has two asymmetrical carbon atoms, so that optical isomers and diastereomers which are based thereon exist. The agent also includes these single isomers or a racemate or diastereomer mixture thereof.

Examples of the pharmaceutically acceptable acid addition salts of the benzylamine derivative represented by General Formula (I) include, but are not limited to, inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; organic sulfonic acid salts such as methanesulfonic acid salt, ethanesulfonic acid salt, benzenesulfonic acid salt, p-toluenesulfonic acid salt and camphorsulfonic acid salt; and the like. More favorable among them are hydrochloric acid salt, hydrobromic acid salt, phosphoric acid salt, tartaric acid salt and methanesulfonic acid salt; and still more favorable are hydrochloric acid salt, tartaric acid salt and methanesulfonic acid salt; but the favorable examples are not limited to these salts above.

Typical preferable examples of the benzylamine derivatives represented by General Formula (I) are shown in Table 2, but the disclosure is not limited to these examples.

TABLE 2

| $R^1$ | $R^2$ | $R^3$ | $R^4$ | $R^5$ |
|---|---|---|---|---|
| Me | Me | Me | H | Me |
| Me | Me | Me | H | $CF_3$ |
| Me | Me | Me | H | OMe |
| Me | Me | Me | H | Cl |
| Me | Me | Me | OMe | Me |
| Me | Me | Me | OMe | $CF_3$ |
| Me | Me | Me | OMe | OMe |
| Me | Me | Me | OMe | Cl |
| Me | Me | $CF_3$ | H | $CF_3$ |
| Me | Me | $CF_3$ | H | OMe |
| Me | Me | $CF_3$ | H | Cl |
| Me | Me | $CF_3$ | OMe | $CF_3$ |
| Me | Me | $CF_3$ | OMe | OMe |
| Me | Me | $CF_3$ | OMe | Cl |
| Me | Me | OMe | H | OMe |
| Me | Me | OMe | H | Cl |
| Me | Me | OMe | OMe | OMe |
| Me | Me | OMe | OMe | Cl |
| Me | Me | Cl | H | Cl |
| Me | Me | Cl | OMe | Cl |

The benzylamine derivatives represented by General Formula (I) can be produced by a method suitable to the characteristics thereof such as the basic skeleton and the kinds of the substituent groups. The starting materials and reagents used for production of these compounds are generally commercially available or can be synthesized by a procedure known by those who are skilled in the art, according to a method described in reference literature such as Peter et al., "Organic Reaction", Wiley & Sons or Fieser, "Fieser and Fieser's Reagent for Organic synthesis" Wiley & Sons and the like.

A typical example of the method of producing the benzylamine derivatives represented by General Formula (I) is that shown in Scheme 1.

Scheme 1

Formual 4

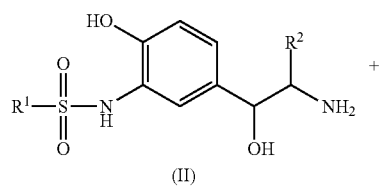

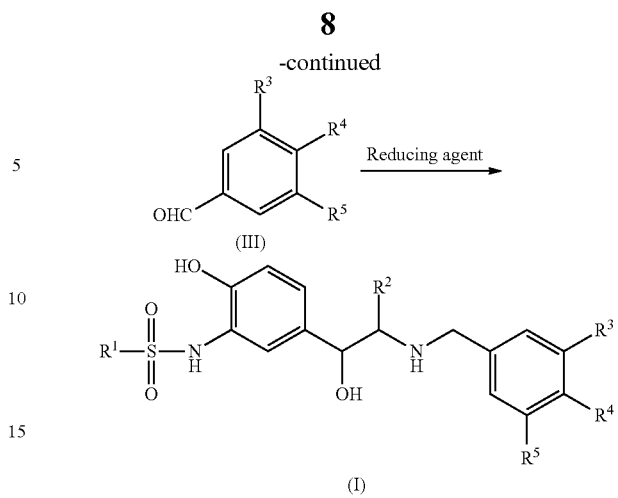

wherein, $R^1$, $R^2$, $R^3$, $R^4$ and $R^5$ are the same as those defined above.

The benzylamine derivative represented by General Formula (I) can be obtained using a method known to those skilled in the art, for example, by reductive alkylation of an amine derivative represented by General Formula (II) with a benzaldehyde derivative represented by General Formula (III).

The solvents that may be used include aprotic polar solvents such as dimethylformamide (DMF), dimethylacetamide and dimethylsulfoxide (DMSO); ether solvents such as diethylether, tetrahydrofuran (THF), dimethoxyethane (DME) and dioxane; hydrocarbon solvents such as benzene, toluene and xylene; halogenated solvents such as dichloromethane, chloroform and 1,2-dichloroethane; alcoholic solvents such as methanol, ethanol and propanol; or the mixed solvents thereof. Normally, use of an alcoholic solvent such as methanol or ethanol, in particular methanol, gives favorable results. The benzaldehyde derivative (III) can be used in an amount of 0.5 to 20 equivalents to the amine derivative (II), but the ratio used normally, 0.5 to 10 equivalents, preferably 0.5 to 3 equivalents.

The reducing agents that may be used include sodium borohydride, sodium cyanoborohydride, sodium triacetoxyborohydride, borane-pyridine complex and the like, and, in particular, sodium cyanoborohydride and borane-pyridine complex are used favorably. The reducing agent can be used in an amount of 0.5 to 50 equivalents to the amine derivative (II), but the ratio used is normally, 1 to 20 equivalents, preferably 1 to 10 equivalents.

A reaction temperature normally of −40 to 150° C., preferably of −30 to 80° C., gives satisfactory results. The reaction time is selected properly according to the conditions such as reaction temperature, but normally a reaction time of 30 minutes to 10 hours gives satisfactory results. The concentration of the amine derivative (II) in the reaction mixture is not particularly limited, but normally, preferably 0.001 to 1 mol/L.

It is possible to convert the benzylamine derivative (I) thus obtained to its acid addition salt by adding an acid to the solution thereof in a suitable solvent. The solvents that may be used include halogenated solvents such as dichloromethane, chloroform and 1,2-dichloroethane; alcoholic solvents such as methanol, ethanol and propanol; ether solvents such as dioxane and diethylether, or the mixed solvents thereof. Normally, use of an alcoholic or ether solvent, in particular methanol, propanol or dioxane, gives favorable results. The amount of the acid added is not particularly limited, but the ratio is within the range of 1 to 30 equivalents with respect to the benzylamine derivative (I), and normally, a ratio of 1 to 10 equivalents, preferably 1 to 5 equivalents, gives satisfactory results.

The amine derivative represented by General Formula (II), which is used as the starting material in Scheme 1, can be obtained, for example, by debenzylation which is a method known to those who are skilled in the art of the amine represented by General Formula (IV), which can be synthesized by the method described in WO 2005/040093, as shown in Scheme 2. The debenzylation is generally carried out by hydrogenolysis in the presence of a metal catalyst.

Scheme 2

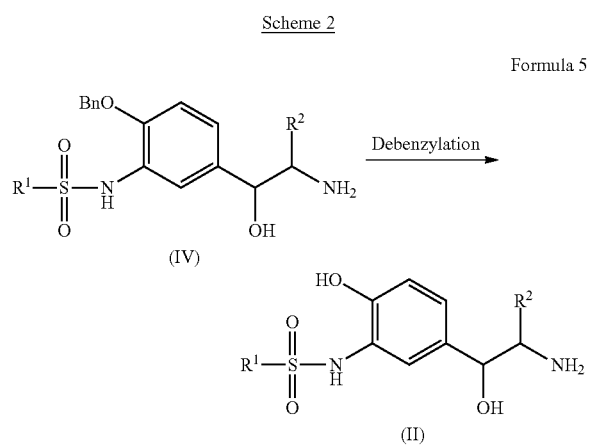

wherein, $R^1$ and $R^2$ are the same as those defined above, and Bn represents a benzyl group.

Use of an alcoholic solvent such as methanol, ethanol or propanol as the reaction solvent gives favorable results. Alternatively, an ether solvent such as tetrahydrofuran (THF), dimethoxyethane (DME) or dioxane may be used as it is, but use of a mixture with an alcoholic solvent such as methanol or ethanol gives favorable results. Catalysts commonly used in hydrogenation reaction, such as platinum oxide, palladium hydroxide and palladium-carbon, can be used as the metal catalysts above, but palladium hydroxide and palladium-carbon are used favorably. The metal catalyst can be used in an amount of 0.001 to 50 equivalents with respect to the amine (IV), but the ratio used is normally 0.05 to 20 equivalents, preferably 0.1 to 5 equivalents. The reaction can be carried out at a reaction temperature of −30 to 80° C., preferably 10 to 50° C., and at a hydrogen pressure of 1 to 100 atmospheres, preferably 1 to 30 atmospheres, but normally, combination of room temperature and normal pressure gives favorable results. The reaction time is selected properly according to the reaction condition, but normally, a reaction time of 30 minutes to 48 hours gives favorable results. The concentration of the substrate (IV) in the reaction mixture is not particularly limited, but normally, preferably 0.001 to 1 mol/L.

The efficacy of treatment to diabetes, obesity, dyslipidemia or metabolic syndrome with the benzylamine derivative represented by General Formula (I) or the pharmaceutically acceptable acid addition salt can be determined by using normal and disease-model animals, such as mice, rats, dogs, and monkeys, (for example, diabetes/obesity model animals described in Takeuchi et al., "Folia Pharmacologica Japonica", 2006, 128, p.37-41 and diabetes/obesity mice described in Winzell M. S. et al., Diabetes, 2004, 53, p. S215-S219), but the test animals are not limited thereto. The fact that the concern about the adverse reactions to the cardiovascular system possibly caused by the benzylamine derivative represented by General Formula (I) or the pharmaceutically acceptable acid addition salt is very limited can be confirmed, for example, by the method described in Salgado et al., Am. J. Physiol. Heart Circ. Phiyol., 2007, 292, p. 593-600, by examining the functions of cardiovascular organs of small animals in the awake state, although the test method is not limited thereto.

Efficacy in treatment of diabetes with the benzylamine derivative represented by General Formula (I) or the pharmaceutically acceptable acid addition salt can be determined, for example, based on clinical symptoms (e.g., blood sugar or plasma glucose concentration), diabetes-related test results (e.g., blood glycated Hemoglobin A1c: HbA1C) or blood sugar in oral glucose tolerance test (OGTT) after two hours. Specifically, compared to individuals to which the benzylamine derivative represented by General Formula (I) or the pharmaceutically acceptable acid addition salt is not administered, individuals having the compound administered likely have advantageous actions such as decrease or improvement in blood sugar or plasma glucose concentration, decrease of blood glycated HbA1C and decrease in the blood sugar in OGTT after two hours. The blood sugar and the plasma glucose concentration can be determined by using a simple blood sugar analyzer, which determines blood sugar, by using a reaction of glucose oxidase, based on the principle of detecting absorbance in colorimetric method or quantitative electrochemical determination (glucose sensor method).

Efficacy of the benzylamine derivative represented by General Formula (I) or the pharmaceutically acceptable acid addition salt in treatment to the diseases with "insulin resistance" can be determined by using, as indicator, the glucose utilization rate or the glucose injection rate of individuals when insulin is injected in glucose clamp test. Insulin tolerance test (ITT) is generally used as a simple and convenient method of evaluating the insulin resistance state of individuals, and specifically, insulin sensitivity is evaluated by using the change in blood sugar under insulin load as an indicator (Tanaka et al., Proc. Natl. Acad. Sci, 2003, 100, P. 15924-15929). Thus, compared to individuals who are not administered with the benzylamine derivative represented by General Formula (I) or the pharmaceutically acceptable acid addition salt, those with the compound administered are possibly alleviated from the state when the blood sugar-decreasing action by insulin deteriorated. In this way, it is possible to make the blood sugar-decreasing action inherent to insulin expressed sufficiently.

Efficacy of the benzylamine derivative represented by General Formula (I) or the pharmaceutically acceptable acid addition salt in treatment of dyslipidemia can be evaluated by using the plasma triglyceride level of individuals as an indicator. Thus, compared to individuals who are not administered with the benzylamine derivative represented by General Formula (I) or the pharmaceutically acceptable acid addition salt, those with the compound administered are likely have advantage of reduced blood triglycerides. Triglycerides can be determined by using a measurement kit of colorimetric method by using a commercially available enzyme reaction.

Efficacy of the benzylamine derivative represented by General Formula (I) or the pharmaceutically acceptable acid addition salt in treatment of obesity can be evaluated by using the body weight, abdominal circumference, body mass index (BMI) or internal fat level of individuals as an indicator. Thus, compared to individuals who are not administered with the benzylamine derivative represented by General Formula (I) or the pharmaceutically acceptable acid addition salt, those with the compound administered are likely lower in the body weight, abdominal circumference, body mass index (BMI) or internal fat level of the individuals.

In addition, the drug containing the benzylamine derivative represented by General Formula (I) or the pharmaceutically acceptable acid addition salt is effective not only to human, but also to mammals other than human, such as mouse, rat, hamster, rabbit, cat, dog, bovine, sheep and monkey.

When the benzylamine derivative represented by General Formula (I) or the pharmaceutically acceptable acid addition salt is used clinically as a therapeutic or prophylactic agent for diabetes, obesity, dyslipidemia or metabolic syndrome, the drug may be the free base or the acid addition salt itself or a mixture thereof with suitable additives such as diluents, stabilizers, preservatives, buffers, solubilizing agents, emulsifiers, diluent and isotonic agents. Examples of the administration forms include oral preparations such as tablets, capsules, granules, powders, and syrups; parenteral preparations such as injections, suppositories and solutions; local administration preparations such as ointments, creams and patches; and the like.

The therapeutic or prophylactic agent for diabetes, obesity, dyslipidemia or metabolic syndrome desirably contains the active ingredient in an amount of 0.00001 to 90 wt %, more preferably 0.0001 to 70 wt %. The amount thereof is selected properly according to the symptom, age, body weight, administration method and the like, but the therapeutic or prophylactic agent can be administered to an adult as the active ingredient in an amount of 0.1 μg to 1 g per day in the case of injection, 1 μg to 10 g in the case of oral preparation, and 1 μg to 10 g in the case of patch, and it can be administered all at once or several times in portions a day.

The benzylamine derivative represented by General Formula (I) or the pharmaceutically acceptable acid addition salt can be used in combination with other diabetes drugs, drugs for treatment of diseases with "insulin resistance," anti-obesity drugs, anti-dyslipidemia drugs, and metabolic syndrome drugs (hereinafter, referred to as combination drugs). The time of administration of the benzylamine derivative represented by General Formula (I) or the pharmaceutically acceptable acid addition salt and the combination drug is not particularly limited, and these drugs may be administered to a patient simultaneously or separately with time difference. The amount of the combination drug administered can be selected properly according to the application clinically used. The blending ratio of the benzylamine derivative represented by General Formula (I) or the pharmaceutically acceptable acid addition salt to the combination drug can be selected properly according to the patient to be administered, administration route, symptom, combination and others.

Examples of the combination drugs used then include insulin preparations (ultrafastacting insulin preparations, fast-acting insulin preparations, mixed insulin preparations, intermediate insulin preparations, long-acting insulin preparations, long-acting soluble insulin preparation, transpulmonary insulin preparation, oral insulin preparation and the like), insulin resistance-improving drugs (pioglitazone, rosiglitazone, netoglitazon, farglitazar, rivoglitazone, balaglitazone and the like), α-glucosidase inhibitors (acarbose, voglibose, miglitol, emiglitate and the like), biguanides (metformin, buformin and the like), sulfonyl ureas (tolbutamide, acetohexamide, chlorpropamide, tolazamide, glyclopyramide, glybuzole, glibenclamide, gliclazide, glimepiride, glipizide, gliquidone and the like), fast-acting insulin secretion stimulators (nateglinide, repaglinide, mitiglinide and the like), GLP-1 agonists (exenatide, liraglutide and the like), amylin agonists (pramlintide and the like), DPP-IV inhibitors (vildagliptin, sitagliptin, saxagliptin, alogliptin, denagliptin and the like), β3 adrenoreceptor agonists (Solabegron, KRP-204, YM-178 and the like), fructose-1,6-bisphosphatase inhibitors (MB-6322, MB-07803 and the like), SGLT (sodium-dependent renal glucose transporter) inhibitors (sergliflozin, AVE-2268, GSK-189075, TS-033, KGA-2727, SAR-7226 and the like), 11β-HSD1 inhibitors (BVT-3498, AMG-221, INCB-13739, INCB-20817 and the like), PTP-1B (protein tyrosine phosphatase-1B) inhibitors (ISIS-113715, JTT-551 and the like), GSK3β (glycogen synthase kinase 2β) inhibitors (SAR-502250 and the like), glucagon antagonists (BAY-27-9955, NN-2501 and the like), glycogen phosphorylase inhibitors (Isofagomine, PSN-357 and the like), CPT1 (carnitine palmitoyltransferase 1) inhibitors (teglicar and the like), glucocorticoid antagonists (mifepristone, KB-3305 and the like), HMG-CoA reductase inhibitors (pravastatin, simvastatin, fluvastatin, atorvastatin, pitavastatin and the like), anion exchange resins (colestyramine, cholestimide and the like), fibrates (clofibrate, clinofibrate, bezafibrate, fenofibrate and the like), nicotinic acid-based drugs (tocopherol nicotinate, CB1 (cannabinoid 1) antagonists, rimonabant, surinabant, MK-0364, AVE-1625 and the like), lipase inhibitors (orlistat and the like), central appetite inhibitors (mazindol, fenfluramine, dexfenfluramine, sibutramine, phentermine and the like) and the like.

EXAMPLES

Hereinafter, our agents and methods will be described specifically with reference to Examples.

Comparative Example 1

N-(5-((1R,2S)-2-Amino-1-hydroxypropyl)-2-hydroxyphenyl)methanesulfonamide (3)

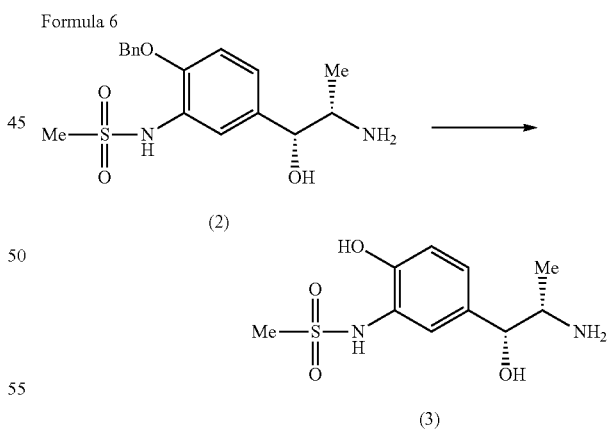

10% palladium/carbon (60 mg) was added to a methanol solution (6 mL) of an amine derivative (2) (195 mg, 0.556 mmol) prepared according to the method described in Comparative Example 1 of WO2005/040093 and the mixture was stirred at room temperature under hydrogen atmosphere for 2.5 hours. The reaction mixture was filtered, and the filtrate was then concentrated, to give a desired amine (3) as a brown solid (153 mg). The desired amine (3) was used in the following step without purification:

¹H NMR (400 MHz, CD₃OD) δ(ppm): 1.15 (d, J=6.8 Hz, 3H), 2.97 (s, 3H), 3.46 (m, 1H), 4.85 (d, J=3.4 Hz, 1H), 6.95 (d, J=8.3 Hz, 1H), 7.14 (dd, J=2.2, 8.3 Hz, 1H), 7.40 (d, J=2.2 Hz, 1H).

Example 1

N-(5-((1R,2S)-2-(3,5-Dimethoxybenzylamino)-1-hydroxypropyl)-2-hydroxyphenyl)methanesulfonamide (4)

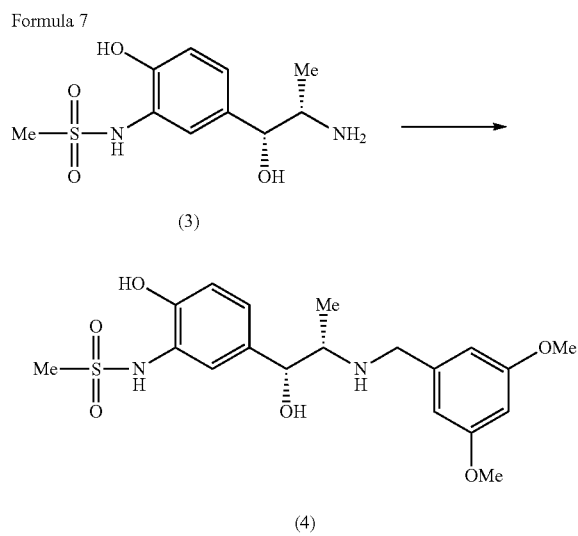

Borane-pyridine complex (445 μL, 4.18 mmol) was added to a methanol solution (10 mL) of an amine (3) (363 mg, 1.39 mmol) and 3,5-dimethoxybenzaldehyde (301 mg, 1.81 mmol), and the mixture was stirred for two hours. The reaction mixture was allowed to cool to room temperature and extracted after addition of water with a mixed solvent (ethyl acetate: methanol=10:1), and the organic layer was washed with saturated aqueous sodium chloride solution. The organic layer was dried and concentrated, and the crude product obtained was purified by amine silica gel column chromatography (eluant:chloroform:methanol=7:1), to give a desired amine (4) as a pale yellow solid (329 mg, yield: 57%).

¹H NMR (400 MHz, CD₃OD) δ(ppm): 1.11 (d, J=6.4 Hz, 3H), 2.83 (m, 1H), 2.89 (s, 3H), 3.61 (d, J=13.2 Hz, 1H), 3.73 (d, J=13.2 Hz, 1H), 3.73 (s, 6H), 4.48 (d, J=6.0 Hz, 1H), 6.34 (t, J=2.4 Hz, 1H), 6.37 (d, J=2.4 Hz, 2H), 6.84 (d, J=8.0 Hz, 1H), 6.99 (dd, J=2.0, 8.0 Hz, 1H), 7.32 (d, J=2.0 Hz, 1H)

4N Hydrogen chloride dioxane solution (0.04 mL) was added to the dioxane solution (1 mL) of the obtained amine (4) (47 mg, 0.11 mmol), and the mixture was freeze-dried, to give hydrochloric acid salt of the amine (4) as white solid (27 mg, yield: 55%).

¹H NMR (400 MHz, DMSOd6) δ(ppm): 1.00 (d, J=6.8 Hz, 3H), 2.91 (s, 3H), 3.23 (m, 1H), 3.76 (s, 6H), 4.18 (m, 2H), 5.13 (br, 1H), 6.03 (d, J=3.6 Hz, 1H), 6.51 (t, J=2.4 Hz, 1H), 6.86 (d, J=2.4 Hz, 2H), 6.92 (d, J=8.0 Hz, 1H), 6.99 (dd, J=2.0, 8.0 Hz, 1H), 7.18 (d, J=2.0 Hz, 1H), 8.78 (s, 1H), 9.10 (br, 1H), 9.19 (br, 1H), 10.0 (s, 1H)

Example 2

N-(5-((1R,2S)-2-(3,5-Bis(trifluoromethyl)benzylamino)-1-hydroxypropyl)-2-hydroxyphenyl)methanesulfonamide (5)

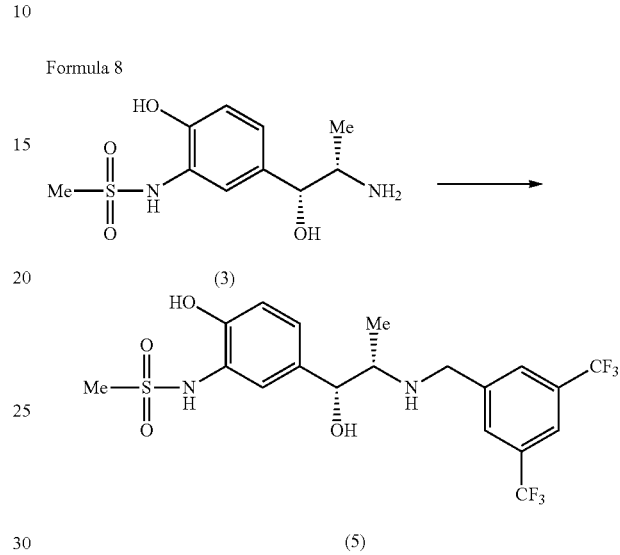

Borane-pyridine complex (130 μL, 1.24 mmol) was added to a methanol solution (4 mL) of an amine (3) (107 mg, 0.41 mmol), 3,5-bis(trifluoromethyl)benzaldehyde (90 μL, 0.54 mmol) at 40° C. and the mixture was stirred for 1.5 hours. The reaction mixture was allowed to cool to room temperature and extracted after addition of water with a mixed solvent (ethyl acetate: methanol=10:1), and the organic layer was washed with saturated aqueous sodium chloride solution. The organic layer was dried and concentrated, and the crude product obtained was purified by amine silica gel column chromatography (eluant:chloroform:methanol=7:1), to give a desired amine (5) as a white solid (132 mg, yield: 66%).

¹H NMR (400 MHz, CD₃OD) δ(ppm): 1.07 (d, J=6.4 Hz, 3H), 2.80 (m, 1H), 2.90 (s, 3H), 3.87 (d, J=14.0 Hz, 1H), 3.95 (d, J=14.0 Hz, 1H), 4.55 (d, J=5.6 Hz, 1H), 6.85 (d, J=8.4 Hz, 1H), 7.02 (dd, J=2.0, 8.0 Hz, 1H), 7.34 (d, J=2.0 Hz, 1H), 7.81 (brs, 1H), 7.89 (brs, 2H)

Example 3

N-(5-((1R,2S)-2-(3,5-Dichlorobenzylamino)-1-hydroxypropyl)-2-hydroxyphenyl)methanesulfonamide (6)

Formula 9

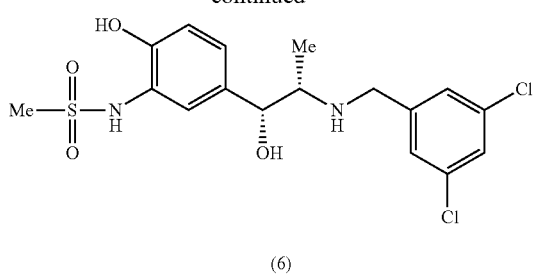

(6)

Borane-pyridine complex (130 μL, 1.21 mmol) was added to an methanol solution (4 mL) of an amine (3) (105 mg, 0.40 mmol) and 3,5-dichlorobenzaldehyde (95 mg, 0.52 mmol) at 40° C. and the mixture was stirred for 1.5 hours. The reaction mixture was allowed to cool to room temperature and extracted after addition of water with a mixed solvent (ethyl acetate: methanol-10:1), and the organic layer was washed with saturated aqueous sodium chloride solution. The organic layer was dried and concentrated, and the crude product obtained was purified by amine silica gel column chromatography (eluant:chloroform:methanol=7:1), to give a desired amine (6) as a white solid (76 mg, yield 45%).

$^1$H NMR (400 MHz, CD$_3$OD) δ(ppm): 1.07 (d, J=6.4 Hz, 3H), 2.76 (m, 1H), 2.91 (s, 3H), 3.67 (d, J=14.0 Hz, 1H), 3.76 (d, J=14.0 Hz, 1H), 4.48 (d, J=5.6 Hz, 1H), 6.86 (d, J=8.4 Hz, 1H), 7.01 (dd, J=2.0, 8.4 Hz, 1H), 7.20 (d, J=2.0 Hz, 2H), 7.29 (t, J=2.0 Hz, 1H), 7.32 (d, J=2.0 Hz, 1H)

Example 4

N-(2-Hydroxy-5-((1R,2S)-1-hydroxy-2-(3,4,5-trimethoxybenzylamino)propyl)phenyl)methane-sulfonamide (7)

Formula 10

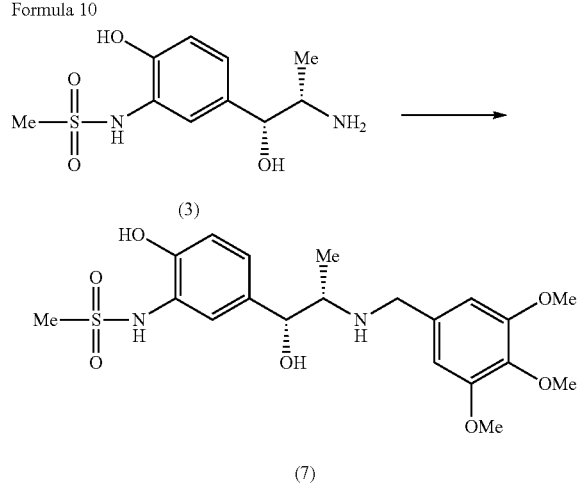

Borane-pyridine complex (135 μL, 1.28 mmol) was added to a methanol solution (4 mL) of an amine (3) (111 mg, 0.43 mmol) and 3,4,5-trimethoxybenzaldehyde (111 mg, 0.55 mmol) at 40° C. and the mixture was stirred for 1.5 hours. The reaction mixture was allowed to cool to room temperature and extracted after addition of water with a mixed solvent (ethyl acetate: methanol=10:1), and the organic layer was washed with saturated aqueous sodium chloride solution. The organic layer was dried and concentrated, and the crude product obtained was purified by amine silica gel column chromatography (eluant:chloroform:methanol=7:1), to give a desired amine (7) as a white solid (67 mg, yield 36%).

$^1$H NMR (400 MHz, CD$_3$OD) δ(ppm): 1.12 (d, J=6.4 Hz, 3H), 2.82 (m, 1H), 2.89 (s, 3H), 3.61 (d, J=12.8 Hz, 1H), 3.72 (s, 3H), 3.73 (d, J=12.8 Hz, 1H), 3.80 (s, 6H), 4.46 (d, J=6.4 Hz, 1H), 6.52 (s, 2H), 6.84 (d, J=8.4 Hz, 1H), 6.99 (dd, J=2.0, 8.4 Hz, 1H), 7.32 (d, J=2.0 Hz, 1H)

Example 5

N-(5-((1R,2S)-2-(3,5-Dimethylbenzylamino)-1-hydroxypropyl)-2-hydroxyphenyl)methanesulfonamide (8)

Formula 11

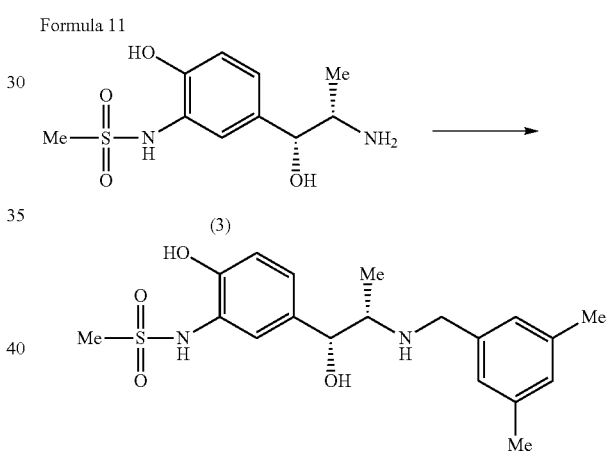

Borane-pyridine complex (160 μL, 1.50 mmol) was added to a methanol solution (5 mL) of an amine (3) (131 mg, 0.50 mmol) and 3,5-dimethylbenzaldehyde (90 μL, 0.65 mmol) at 40° C. and the mixture was stirred for 1.5 hours. The reaction mixture was allowed to cool to room temperature and extracted after addition of water with a mixed solvent (ethyl acetate: methanol=10:1), and the organic layer was washed with saturated aqueous sodium chloride solution. The organic layer was dried and concentrated, and the crude product obtained was purified by amine silica gel column chromatography (eluant:chloroform:methanol=7:1), to give a desired amine (8) as a white solid (62 mg, yield 33%).

$^1$H NMR (400 MHz, CD$_3$OD) δ(ppm): 1.10 (d, J=6.4 Hz, 3H), 2.25 (s, 6H), 2.82 (m, 1H), 2.88 (s, 3H), 3.60 (d, J=12.8 Hz, 1H), 3.73 (d, J=12.8 Hz, 111), 4.49 (d, J=6.0 Hz, 1H), 6.79 (brs, 2H), 6.84 (d, J=8.4 Hz, 1H), 6.87 (brs, 1H), 6.98 (dd, J=2.0, 8.4 Hz, 1H), 7.31 (d, J=2.0 Hz, 1H)

Example 6

N-(5-((1R,2S)-2-(3,5-Diethoxybenzylamino)-1-hydroxypropyl)-2-hydroxyphenyl)methanesulfonamide (9)

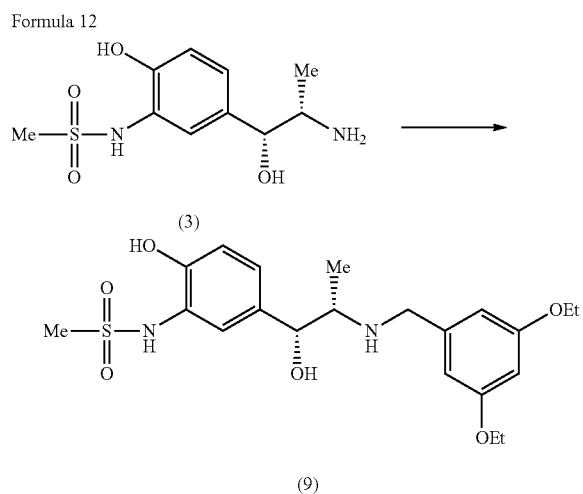

Borane-pyridine complex (155 μL, 1.46 mmol) was added to a methanol solution (3.3 mL) of an amine (3) (127 mg, 0.486 mmol) and 3,5-diethoxybenzaldehyde (123 mg, 0.632 mmol) at 40° C. and the mixture was stirred for 2.5 hours. The reaction mixture was allowed to cool to room temperature and extracted after addition of water with a mixed solvent (ethyl acetate: methanol=10:1), and the organic layer was washed with saturated aqueous sodium chloride solution. The organic layer was dried and concentrated, and the crude product obtained was purified by amine silica gel column chromatography (eluant:chloroform:methanol=7:1), to give a desired amine (9) as a yellow solid (114 mg, yield 54%).

$^1$H NMR (400 MHz, CD$_3$OD) δ(ppm): 1.14 (d, J=6.4 Hz, 3H), 1.39 (t, J=7.1 Hz, 6H), 2.88 (m, 1H), 2.93 (s, 3H), 3.63 (d, J=12.9 Hz, 1H), 3.76 (d, J=12.9 Hz, 1H), 3.99 (q, J=7.1 Hz, 4H), 4.52 (d, J=5.9 Hz, 1H), 6.35 (t, J=2.0 Hz, 1H), 6.38 (d, J=2.0 Hz, 2H), 6.88 (d, J=8.3 Hz, 1H), 7.02 (dd, J=2.0, 8.3 Hz, 1H), 7.36 (d, J=2.0 Hz, 1H)

Example 7

Evaluation of Agonistic Activity for Human β Adrenoreceptor

1. Test method

The test was performed according to the method described in the literature of Chaudhry and Granneman (J. Pharmacol Exp. Ther., 1994, 271, p. 1253) or Hoffmann et al. (Naunyn-Schmiedeberg's Arch. Pharmacol., 2004, 369, p. 151). Human β3 adrenoreceptor agonistic activity was evaluated by using SK-N-MC cells in the presence of a β1 adrenoreceptor-selective antagonist (CGP-20712A, 1 μM). Human β2 and β1 adrenoreceptor agonistic activity was evaluated by using CHO-K1 cells in which the receptors are stably expressed. Alpha Screen cAMP Detection Kit (6760625, Perkin Elmer), which uses the change of cAMP production as indicator, was used for evaluation of the agonistic activity in all cases. Various cells were cultured in culture flasks, and the cells were separated and collected by EDTA/PBS treatment on the test day and diluted with a stimulus buffer (0.1% BSA, 500 μM IBMX, 5 mM HEPES, HBSS, pH 7.4) to a cell concentration of 10,000 cells/well. Standard solution (cAMP) or a compound solution of Example was added onto a 384-well plate (Optiplate New, #6007290, Perkin Elmer) in an amount of 5 μL to the final concentration ($10^{-10}$ to $10_{-4}$) and then, 5 μL of anti-cAMP acceptor beads or a cell/Anti-cAMP acceptor beads mixture solution was added thereto, and the mixture was allowed to react at 37° C. in a dark place for 30 minutes. After reaction, biotinylated-cAMP/streptavidin donor beads prepared in a lysis buffer (0.1% BSA, 0.3% Tween-20, 5 mM HEPES, pH 7.4) were added in an amount of 15 μL, and the mixture was allowed to react at room temperature in a dark place for 60 minutes, and the AlphaScreen signals (cps) from the mixture was determined with Fusion a (Packard Bio-Science). In data analysis, the reaction rate of the compound of each Example was first calculated, based on 100% of the maximum amount of cAMP produced by isoproterenol, and pEC50 value (negative common logarithm of 50% reaction concentration towards isoproterenol) was calculated by linear regression. When the reaction of the compound of Example did not proceed to a degree of 50% at the highest concentrations, the result was expressed by n.d. (not detected), and when the reaction of the compound of Example did not proceed to a degree of 50% in some of the tests, the average of the pEC50 values that could be calculated was used as the pEC50 value of the compound of Example.

2. Results

All of the compounds of Examples 1 to 5 activated the human β3 adrenoreceptor (Table 3).

In addition, the compounds of Examples 1 to 5 were all superior in selectivity to β3 adrenoreceptor and were considered to have similar properties.

TABLE 3

| Compound | β3 | β2 | β1 |
| --- | --- | --- | --- |
| Compound of Example 1 | 7.40 | 5.63 | n.d. |
| Compound of Example 2 | 7.50 | n.d. | n.d. |
| Compound of Example 3 | 7.66 | 5.97 | n.d. |
| Compound of Example 4 | 7.48 | n.d. | n.d. |
| Compound of Example 5 | 7.14 | n.d. | n.d. | n.d.: not detected at 10 μM

Example 8

Evaluation of Efficacy by using Type 2 Diabetes-Model Mice (KK/Ay Mice)

1. Test Method

KK/Ay male mice of 5 weeks of age (CLEA Japan, Inc.) were purchased; a feeding stuff for growth CMF (Oriental Yeast) was provided since the day of arrival; and mice after growth for 3 weeks or longer were used. The compound of Example 1 was diluted to 2 mg/mL, as it is dissolved in physiological saline, and the solution was administered subcutaneously in an amount of 5 mL/kg, by using a disposable syringe (Terumo) and a 26G injection needle (Terumo). Physiological saline was administered to the mice in the vehicle group. The solution was administered once a day from the day of first administration (day 0) to day 13, and the tail vein was cut open with a knife (disposable scalpel, FEATHER) and the blood sugar was determined with a simplified blood sugar analyzer (MediSense Precision Xceed, Abotto Japan). Statistical treatment of the individual data obtained was carried out by a two-group test (unpaired t-test).

2. Results

The compound of Example 1 lowered the blood sugar statistically significantly, compared to the solvent group (Table 4). The result indicates that the compound of Example 1 is effective to type 2 diabetes.

TABLE 4

| Compound | Blood sugar (mg/mL) |
|---|---|
| Vehicle | 456 ± 21 |
| Compound of Example 1, 10 mg/kg | 336 ± 33** |

**$p < 0.01$ vs. vehicle administration group (unpaired t-test)

Example 9

Evaluation of Efficacy by using Diabetes/Obesity-Model Mice (DIO Mice)

1. Test Method

C57BL/6J mice grown on a solid feeding stuff containing 60% fat (D12492, Research Diets) since 4 weeks of age, (male, Charles River Laboratories, Japan, 13 weeks of age) were purchased and mice of 16 weeks of age grown on D12492 since the day of arrival were used. C57BL/6J mice of 16 weeks of age grown on normal food since the day of arrival were used in the normal group. The compound of Example 1 was diluted to 2 mg/mL or 0.6 mg/mL, as it is dissolved in physiological saline, and the solution was administered subcutaneously in an amount of 5 mL/kg, by using a disposable syringe (Terumo) and a 26G injection needle (Terumo). Physiological saline was administered in the vehicle group. The solution was administered once a day from the day of first administration (day 0) to day 26. The body weight was determined on day 26; the tail vein was cut open with a knife (disposable scalpel, FEATHER); and the blood sugar was determined with a simplified blood sugar analyzer (MediSense Precision Xceed, Abotto Japan).

The blood was collected (approximately 70 μL) from the same site by using a heparin-treated capillary (Hematokrit Kapilaren, 75 μL, HIRSCMANN LABORGERATE) and the collected blood was centrifuged (12,000 rpm, 7 min, 4° C.) in a hematocrit centrifuge (KUBOTA3100, Kubota Corp.) and the plasma was stored, as it is frozen in an Eppendorf tube, until it is used for measurement of triglyceride. The triglyceride measurement was carried out by using Triglyceride E-Test Wako (Wako Pure Chemical Industries). Four μL of the sample was added to 250 μL of the coloring liquid, after reaction at 37° C. for 1 hour, and the absorbance (595 nm) of the mixture was determined by using a microplate reader (Bio-Rad, Model 680). Separately, insulin tolerance test (ITT) was performed on day 27.

The mouse was left non-feeded in a fasting cage after drug administration on day 26. In the morning of the day of ITT (day 27), the fasting blood sugar was determined by a method identical with that used for blood sugar measurement on day 26. The blood sugar was measured once again in the afternoon of the same day; an insulin solution was administered intraperitoneally (0.3 unit/5 mL/kg) immediately after then; and the blood sugar was measured 30, 60, 120 and 180 minutes after insulin administration since then. The insulin solution was prepared by diluting 100 unit/mL solution (Humalin R injection, Eli Lilly) with 0.1% BSA-containing physiological saline to a concentration of 0.06 unit/mL.

The insulin level was measured by using an insulin measurement kit (Lebis Insulin Mouse U, Shibayagi). Finally, HOMA-IR was also calculated from the values of fasting blood sugar and fasting insulin. The weight of the fat around the mouse testicles was also determined after measurement of ITT. Statistical treatment of the individual data obtained was carried out by a two-group test (unpaired t-test) or a multiplex comparison test (parametric Williams test).

2. Results (1) Efficacy in Treatment of Diabetes

The compound of Example 1 exhibited a significant blood sugar-reducing effect even on DIO mice, which are known to be non-severe type-2 diabetes model mice (Table 5).

TABLE 5

| Compound | Blood sugar (mg/mL) |
|---|---|
| Normal mounse | |
| Vehicle | 172 ± 7 |
| DIO mouse | |
| Vehicle | 206 ± 6[###] |
| Compound of Example 1, 3 mg/kg | 177 ± 9* |
| Compound of Example 1, 10 mg/kg | 168 ± 8* |

[##]$p < 0.01$ vs. normal mice in vehicle administration group (unpaired t-test),
*$p < 0.05$ vs. DIO mice in vehicle administration group (parametric Williams test)

(2) Efficacy in Treatment of Obesity

Significant suppression of increase in body weight was observed in the mice in the group with the compound of Example 1 administered, compared to those in the vehicle group. The weight of the fat around the mouse testicles, which is known as a parameter of internal fat, also declined significantly (Table 6). The results above indicate that the compound of Example 1 is effective to obesity.

TABLE 6

| Compound | Increase in body weight (g) | Weight of the fat around the mouse testicles (g) |
|---|---|---|
| Normal mouse | | |
| Vehicle | 0.0 ± 0.2 | 0.5 ± 0.1 |
| DIO mouse | | |
| Vehicle | 4.4 ± 0.6[###] | 2.6 ± 0.1[###] |
| Compound of Example 1, 3 mg/kg | 3.5 ± 0.6 | 2.6 ± 0.1[###] |
| Compound of Example 1, 10 mg/kg | 2.1 ± 0.5** | 2.3 ± 0.1* |

[###]$p < 0.001$ vs. normal mice in vehicle administration group (unpaired t-test),
*$p < 0.05$ and **$p < 0.01$ vs. DIO mice in vehicle administration group (parametric Williams test)

(3) Insulin Tolerance Test (ITT)

Blood sugar declined statistically significantly in the mice in the group with the compound of Example 1 administered, compared to those in the vehicle group (FIG. 1). The results indicate that the compound of Example 1 is effective to diseases with "insulin resistance".

(4) Efficacy in Treatment of Dyslipidemia

Plasma triglyceride (TG) declined statistically significantly in the mice in the group with the compound of Example 1 administered, compared to those in the vehicle group (Table 7). The results indicate that the compound of Example 1 is effective to dyslipidemia.

TABLE 7

| | DIO mouse |
| --- | --- |
| Compound | Triglyceride (mg/dL) |
| Vehicle | 164 ± 14 |
| Compound of Example 1, 3 mg/kg | 162 ± 14 |
| Compound of Example 1, 10 mg/kg | 129 ± 9* |

*$p < 0.05$ vs. vehicle administration group (parametric Williams test)

As described above, Examples 8 and 9 indicate that the benzylamine derivatives represented by General Formula (I), which is represented by the compound of Example 1, are therapeutically effective not only to diabetes, but also to obesity and dyslipidemia. The fact that they additionally have action to lower blood sugar and TG and are therapeutically effective to obesity (have action to decrease fat and body weight) indicates that they are also therapeutically effective to metabolic syndrome.

Example 10

Evaluation of the Effect on the Cardiovascular System of Conscious Rat

1. Test Method

SD male rats of 7 weeks of age (Charles River Laboratories Japan Inc.) were purchased and used when they are 8 weeks of age. The rats were anesthetized by intraperitoneal administration of pentobarbital at 60 mg/kg; the back central region and the femoral region were cut open; a polyethylene tube (SP-31, Natsume Seisakusho Co., Ltd.) connected to a polyurethane tube (BC-3.5P, American Access Technologies) was inserted from the back to the femoral region, to place the polyethylene tube in femoral artery. After the femoral region was sutured, a flexible stainless steel pipe containing the polyethylene tube was sutured and fixed to the back skin. Heparin at 100 IU to 200 IU/mL was filled into the polyethylene tube and the polyurethane tube for prevention of blood clotting. After surgical operation, the rats were placed and grown back in 5-compartment wire mesh cage. The rats in the awake state were placed in a wire mesh cage surrounded by polystyrene foam board on the following day, a three-way cock attached to the polyurethane tube on the back was connected to a tube for measurement of blood pressure attached to a Life Kit for monitoring blood pressure (DX-360, Nihon Kohden Corp.).

The heart rate of the rats was determined, by sending the pulse wave obtained in the blood pressure amplifier (AP-641G, Nihon Kohden Corp.) attached to the Life Kit for monitoring blood pressure to an instantaneous heart rate meter unit (AT-601T, Nihon Kohden Corp.). The heart rate was recorded on the chart paper in a thermal multirecorder (RIA-1300A, Nihon Kohden Corp.) by using a polygraph (RM-6000, Nihon Kohden Corp.).

After confirmation that the rat heart rate was stabilized, physiological saline (vehicle) was administered with a needed previously connected to the subcutaneously inserted tube in an amount of 1 mL/kg$_i$ to the rats in the vehicle administration group, and 1 mg/mL physiological saline solution of the compound of Example 1 was administered in an amount of 1 mL/kg to the rats in the group with the compound of Example 1 administered. The time of each administration was test-starting time. In addition, 1 mL/kg physiological saline was administered to the rats in the vehicle administration group at an interval of 30 minutes from the test starting time, while 3 mg/mL or 10 mg/mL physiological saline solution of the compound of Example 1 was administered in an amount of 1 mL/kg to the rats in the group with the compound of Example 1 administered at an interval of 30 minutes from the test starting time, and change in heart rate after administration was monitored. In statistical analysis of the individual data obtained, the vehicle administration group and the group with the compound of Example 1 administered were compared at each point by a two-group test (unpaired t-test).

2. Results

Figure 2:
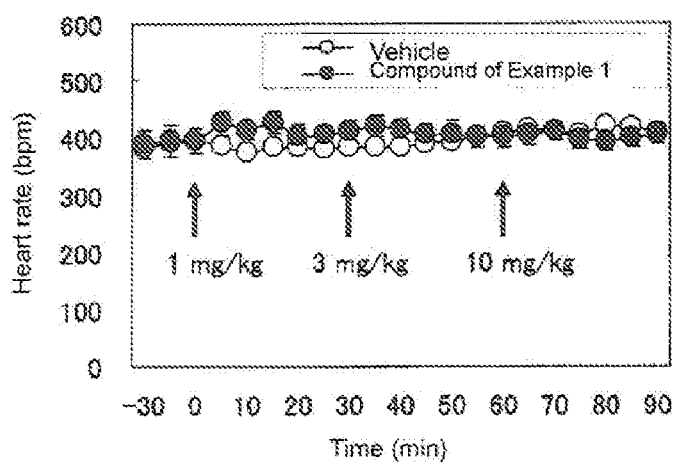
FIG. 2 is a chart showing the influence of the compound of Example 1 on the hear rate of conscious rat. The abscissa shows the period (minutes) after drug administration, while the ordinate shows the heart rate of rat.

The compound of Example 1 did not have any influence on rat heart rate, similarly to the vehicle (FIG. 2). The results above indicate that there is very limited concern about the compound of Example 1 showing any adverse influence on the heart rate of cardiovascular system.

Example 11

Evaluation of the Effect on Electrocardiogram of Anesthetized Dog

1. Test Method

A male beagle and a female beagle of 11 months of age were used in the test. A beagle was anesthetized by intravenous administration of thiopental sodium at 25 mg/kg, and fixed at the dorsal position under anesthesia by isoflurane inhalation with oxygen-nitrous oxide gas (1:1). Artificial respiration was carried out under the condition of 20 mL/kg and 15 times/minute. In measurement of the electrocardiogram, bipolar extremity leads (I, II and III) and augmented unipolar extremity leads (aVR, aVL and aVF) were recorded and QT interval determined by using an electrocardiogram analyzer for animals (α6000AX-D, Fukuda M-E Kogyo Co., Ltd.), as needle electrodes were placed on four extremities.

The QTc value was calculated according to the Fridericia's formula:

$$QTc = QT/\sqrt[3]{(R-R)}.$$

For observation of arrhythmia in electrocardiographic waveform during test, compression electrocardiogram was printed out from the small memory card by using a long-term electrocardiogram analyzer (HS1000 system, Fukuda M-E Kogyo Co., Ltd.). The samples of the compound of Example 1 were prepared by dissolving the compound in physiological saline at concentrations of 12 mg/mL, 4 mg/mL and 1.2 mg/mL. After confirmation of stabilization of the electrocardiogram, the sample was administered through a needle (22G) previously placed in the side forearm subcutaneous vein, by using an automatic injector (Harvard digital infusion pump MODEL-22, HARVARD APPAPATUS) over a period of 10 minutes.

First, vehicle (physiological saline) was administered in an amount of 0.5 mL/kg and then, after 35 minutes, 1.2 mg/mL physiological saline solution of the compound of Example 1 was administered in an amount of 0.5 mL/kg. Additionally, 4 mg/mL or 12 mg/mL physiological saline solution of the compound of Example 1 was administered in an amount of 0.5 mL/kg at an interval of 65 minutes after administration. The QT interval and the QTc value were measured, in each administration above, 5 minutes before administration, immediately before start of administration, as well as 5, 10, 15 and 30 minutes after start of administration. Thus, the measured value 30 or 60 minutes after start of previous administration corresponds to the value 5 minutes before start of administration for the following application.

2. Results

The compound of Example 1 did not cause prolongation of the QT interval in any application and there was no arrhythmia observed in electrocardiographic waveform in any application (Table 8).

TABLE 8

| Compound | Dosage | After administration (minute) | Individual 1 (male) QT interval | QTc | Individual 2 (female) QT interval | QTc |
| --- | --- | --- | --- | --- | --- | --- |
| Solvent (physiological saline) | 0.5 mL/kg/ 10 min | −5 | 251 | 313 | 245 | 290 |
| | | 0 | 256 | 317 | 245 | 290 |
| | | 5 | 255 | 318 | 245 | 291 |
| | | 10 | 245 | 306 | 245 | 292 |
| | | 15 | 251 | 313 | 245 | 293 |
| | | 30 | 245 | 305 | 240 | 293 |
| Compound of Example 1 | 0.6 mg/kg/ 10 min | 0 | 241 | 303 | 240 | 293 |
| | | 5 | 228 | 299 | 243 | 315 |
| | | 10 | 210 | 287 | 236 | 310 |
| | | 15 | 205 | 280 | 223 | 296 |
| | | 30 | 213 | 290 | 218 | 297 |
| | | 45 | 220 | 296 | 211 | 288 |
| | | 60 | 221 | 294 | 213 | 292 |
| | 2 mg/kg/ 10 min | 0 | 218 | 293 | 215 | 293 |
| | | 5 | 203 | 283 | 210 | 292 |
| | | 10 | 203 | 283 | 210 | 289 |
| | | 15 | 213 | 294 | 210 | 288 |
| | | 30 | 218 | 297 | 225 | 303 |
| | | 45 | 221 | 299 | 220 | 298 |
| | | 60 | 225 | 304 | 221 | 299 |
| | 6 mg/kg/ 10 min | 0 | 220 | 296 | 220 | 296 |
| | | 5 | 210 | 292 | 215 | 293 |
| | | 10 | 211 | 294 | 211 | 289 |
| | | 15 | 210 | 291 | 215 | 292 |
| | | 30 | 211 | 291 | 213 | 289 |
| | | 45 | 235 | 320 | 226 | 303 |
| | | 60 | 226 | 305 | 220 | 294 |

As described above, the results in Examples 10 and 11 suggest that the benzylamine derivatives represented by General Formula (I), which are represented by the compound of Example 1 are quite unlikely to cause adverse reactions on the circulatory system such as increase of heart rate and expansion of QT, which were concerned for conventional β3 adrenoreceptor agonists.

INDUSTRIAL APPLICABILITY

The new benzylamine derivatives or the pharmaceutically acceptable acid addition salts can be used in drugs containing it as active ingredient, in particular in therapeutic or prophylactic agents for diabetes, obesity, dyslipidemia or metabolic syndrome.

The invention claimed is:

1. A method of treatment of diabetes, obesity, dyslipidemia or metabolic syndrome, comprising administering an effective amount of a benzylamine derivative represented by Formula (I):

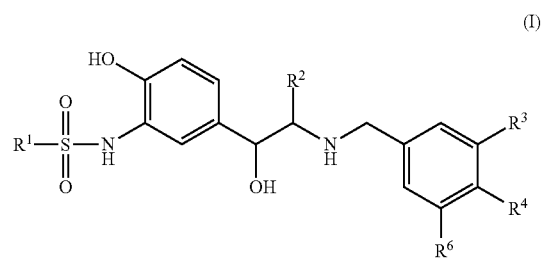

wherein, $R^1$ represents an alkyl group having 1 to 6 carbon atoms; $R^2$ represents an alkyl group having 1 to 6 carbon atoms; $R^3$ and $R^5$ each independently represent a halogen atom, an alkyl group having 1 to 6 carbon atoms, a haloalkyl group having 1 to 6 carbon atoms or an alkoxy group having 1 to 6 carbon atoms; and $R^4$ represents a hydrogen atom or an alkoxy group having 1 to 6 carbon atoms, or a pharmaceutically acceptable acid addition salt thereof.

2. The method according to claim 1, wherein:
$R^1$ represents methyl, ethyl, propyl, isopropyl or tert-butyl; and
$R^2$ represents methyl, ethyl, propyl or isopropyl.

3. The method according to claim 1, wherein:
$R^3$ and $R^5$ each independently represent methyl, ethyl, fluoromethyl, difluoromethyl, trifluoromethyl, methoxy, ethoxy or chloro; and
$R^4$ represents hydrogen, methoxy, ethoxy, propoxy or isopropoxy.

4. The method according claim 1, wherein:
$R^2$ represents methyl;
$R^3$ and $R^5$ each independently represents methyl, ethyl, fluoromethyl, difluoromethyl, trifluoromethyl, methoxy, ethoxy or chloro; and
$R^4$ represents hydrogen, methoxy, ethoxy, propoxy or isopropoxy.

5. The method according to claim 1, wherein:
$R^1$ and $R^2$ each represent methyl;
$R^3$ and $R^5$ each independently represent methyl, trifluoromethyl, methoxy or chloro; and
$R^4$ represents hydrogen or methoxy.

6. The method according to claim 1, wherein:
$R^1$ and $R^2$ each represent methyl;
$R^3$ and $R^5$ each represent methyl, trifluoromethyl, methoxy or chloro simultaneously; and
$R^4$ represent hydrogen.

7. The method according to claim 2, wherein:
$R^3$ and $R^5$ each independently represent methyl, ethyl, fluoromethyl, difluoromethyl, trifluoromethyl, methoxy; ethoxy or chloro; and
$R^4$ represents hydrogen, methoxy, ethoxy, propoxy or isopropoxy.

8. The method according to claim 2, wherein:
$R^2$ represents methyl;
$R^3$ and $R^5$ each independently represents methyl, ethyl, fluoromethyl, difluoromethyl, trifluoromethyl, methoxy, ethoxy or chloro; and
$R^4$ represents hydrogen, methoxy, ethoxy, propoxy or isopropoxy.

9. The method according to claim 3, wherein:
$R^2$ represents methyl;
$R^3$ and $R^5$ each independently represents methyl, ethyl, fluoromethyl, difluoromethyl, trifluoromethyl, methoxy, ethoxy or chloro; and $R^4$ represents hydrogen, methoxy, ethoxy, propoxy or isopropoxy.

10. The method according to claim 7, wherein:
$R^2$ represents methyl;
$R^3$ and $R^5$ each independently represents methyl, ethyl, fluoromethyl, difluoromethyl, trifluoromethyl, methoxy, ethoxy or chloro; and
$R^4$ represents hydrogen, methoxy, ethoxy, propoxy or isopropoxy.

11. The method according to claim 2, wherein:
$R^1$ and $R^2$ each represent methyl;
$R^3$ and $R^5$ each independently represent methyl, trifluoromethyl, methoxy or chloro; and
$R^4$ represents hydrogen or methoxy.

12. The method according to claim 3, wherein:
$R^1$ and $R^2$ each represent methyl;
$R^3$ and $R^5$ each independently represent methyl, trifluoromethyl, methoxy or chloro; and
$R^4$ represents hydrogen or methoxy.

13. The method according to claim 4, wherein:
$R^1$ and $R^2$ each represent methyl;
$R^3$ and $R^5$ each independently represent methyl, trifluoromethyl, methoxy or chloro; and
$R^4$ represents hydrogen or methoxy.

* * * * *

UNITED STATES PATENT AND TRADEMARK OFFICE
CERTIFICATE OF CORRECTION

Page 1 of 1

PATENT NO. : 8,198,330 B2
APPLICATION NO. : 13/056201
DATED : June 12, 2012
INVENTOR(S) : Hasebe et al.

It is certified that error appears in the above-identified patent and that said Letters Patent is hereby corrected as shown below:

In Column 18

At line 9, please change "$10_{-4}$" to --$10^{-4}$--

Signed and Sealed this
Twenty-third Day of October, 2012

David J. Kappos
*Director of the United States Patent and Trademark Office*